(12) United States Patent
Christie (10) Patent No.: US 11,484,106 B2
(45) Date of Patent: Nov. 1, 2022

(54) IMPLANT FOR REMOVABLE PROSTHETIC NAIL

(71) Applicant: Drew Christie, Indianapolis, IN (US)

(72) Inventor: Drew Christie, Indianapolis, IN (US)

( * ) Notice: Subject to any disclaimer, the term of this patent is extended or adjusted under 35 U.S.C. 154(b) by 420 days.

(21) Appl. No.: 16/687,775

(22) Filed: Nov. 19, 2019

(65) Prior Publication Data

US 2021/0145146 A1 May 20, 2021

(51) Int. Cl.
| | |
|---|---|
| *A45D 29/00* | (2006.01) |
| *A61F 5/11* | (2006.01) |
| *A61F 2/42* | (2006.01) |
| *A45D 31/00* | (2006.01) |
| *A61F 2/58* | (2006.01) |

(52) U.S. Cl.
CPC ............ *A45D 29/00* (2013.01); *A61F 2/4241* (2013.01); *A61F 5/11* (2013.01); *A45D 31/00* (2013.01); *A61F 2/586* (2013.01)

(58) Field of Classification Search
CPC ................................... A61F 5/11; A61F 2/586
See application file for complete search history.

(56) References Cited

U.S. PATENT DOCUMENTS

| | | | |
|---|---|---|---|
| 4,445,234 A | 5/1984 | Ogunro | |
| 4,559,055 A | 12/1985 | Ogunro | |
| 5,060,678 A | 10/1991 | Bauman et al. | |
| 7,338,523 B2 | 3/2008 | Brodkin | |
| 7,357,816 B2 | 4/2008 | Brodkin | |
| 8,337,443 B2 * | 12/2012 | Harada | A61F 5/11 602/30 |
| 8,641,761 B2 | 2/2014 | Bauman et al. | |
| 2007/0100451 A1 * | 5/2007 | Brodkin | A61F 5/11 623/57 |
| 2011/0257570 A1 * | 10/2011 | Erdogan | A61F 5/11 602/5 |

* cited by examiner

*Primary Examiner* — Javier G Blanco
(74) *Attorney, Agent, or Firm* — Woodard Emhardt Henry Reeves & Wagner LLP

(57) ABSTRACT

An assembly for mounting a prosthetic nail for a human or animal digit. The assembly includes at least one transdermal anchor with an interior portion and an exterior portion. The interior portion may be positioned within tissue of the digit, and the exterior portion may extend outside the tissue of the digit. In another aspect, an exterior base may be positioned on a nail bed of the digit, and the exterior base may be coupled to the exterior portion of the transdermal anchor. The base may include a mount for removably a prosthetic nail to the base.

12 Claims, 7 Drawing Sheets

IMPLANT FOR REMOVABLE PROSTHETIC NAIL

BACKGROUND

This application generally relates to an apparatus and method of mounting prosthetic nails.

SUMMARY

Disclosed is an assembly for mounting a prosthetic nail for a human or animal digit, such as in the case of mounting a prosthetic nail to a human finger or toe. The system includes at least one transdermal anchor with an interior portion and an exterior portion. The interior portion may be positioned within tissue of the digit, and the exterior portion extends outside the tissue of the digit. In another aspect, an exterior base may be positioned on a nail bed of the digit, and the exterior base may be coupled to the exterior portion of the transdermal anchor. In another aspect, the exterior base may include a mount for coupling the base to a prosthetic nail.

In another aspect, the interior portion may define a through opening for capturing surrounding tissue of the digit. The interior portion may optionally define multiple through openings, and one of the through openings may be tear-drop shaped. The interior portion optionally includes an arcuate extension at a proximal end of the interior portion for capturing surrounding tissue. The interior portion may include an angled section angled outwardly to offset a remaining section of the interior portion away from a distal phalanx of the digit. The interior portion is optionally free from direct bone contact in the digit.

In another aspect, the transdermal anchor may be made of a material that includes a rigid polymeric material. The transdermal anchor is optionally made primarily of polyetheretherketone.

In another aspect, the exterior base mount optionally includes protrusions extending away from the base that are arranged to engage multiple couplers on the prosthetic nail. The protrusions optionally include multiple portions at right angles to each other.

In another aspect, the exterior base includes couplers for engaging corresponding retention members at a distal end of the external portion of the transdermal anchor. The exterior base portion is optionally made of a base material that includes a pliable polymeric material. In another aspect, the system includes a layer of pliable polymeric material that may surround the prosthetic nail and may be positioned between the prosthetic nail and the mount.

In another aspect, the apparatus includes one or more additional transdermal anchors adjacent to the nail. The one or more additional transdermal anchors may have an interior portion and an exterior portion, the interior portion is positioned within tissue of the digit, and the exterior portion extends outside the tissue of the digit.

Also disclosed is a transdermal anchor for a mount assembly that includes a transdermal anchor with an interior portion and an exterior portion. The interior portion may be positioned within tissue of a digit, and the exterior portion optionally extends outside the tissue of the digit. The interior portion may define a through opening for capturing surrounding tissue of the digit.

In another aspect, the interior portion optionally defines multiple through openings, and one of the through openings is tear-drop shaped. The interior portion optionally includes an angled section angled outwardly to offset a remaining section of the interior portion away from a distal phalanx of the digit. In another aspect, the interior portion is optionally free from direct bone contact in the digit. In another aspect, the interior portion includes an optional arcuate extension at a proximal end of the interior portion for capturing surrounding tissue. In another aspect, the transdermal anchor may be made of a material that includes a rigid polymeric material, or may be made primarily of polyetheretherketone.

In another aspect, the transdermal anchor may include an exterior base positioned on a nail bed of the digit. The Exterior base is optionally coupled to the exterior portion of the transdermal anchor. In another aspect, the exterior base may include a mount for coupling the base to a prosthetic nail. The mount of the exterior base optionally includes protrusions extending away from the base that may be arranged to engage multiple couplers on the prosthetic nail. In another aspect, the protrusions may include multiple portions at right angles to each other. In another aspect, the exterior base optionally includes couplers for engaging corresponding retention members at a distal end of the external portion of the transdermal anchor.

Further forms, objects, features, aspects, benefits, advantages, and embodiments of the present invention will become apparent from a detailed description and drawings provided herewith.

DETAILED DESCRIPTION

Figure 1:
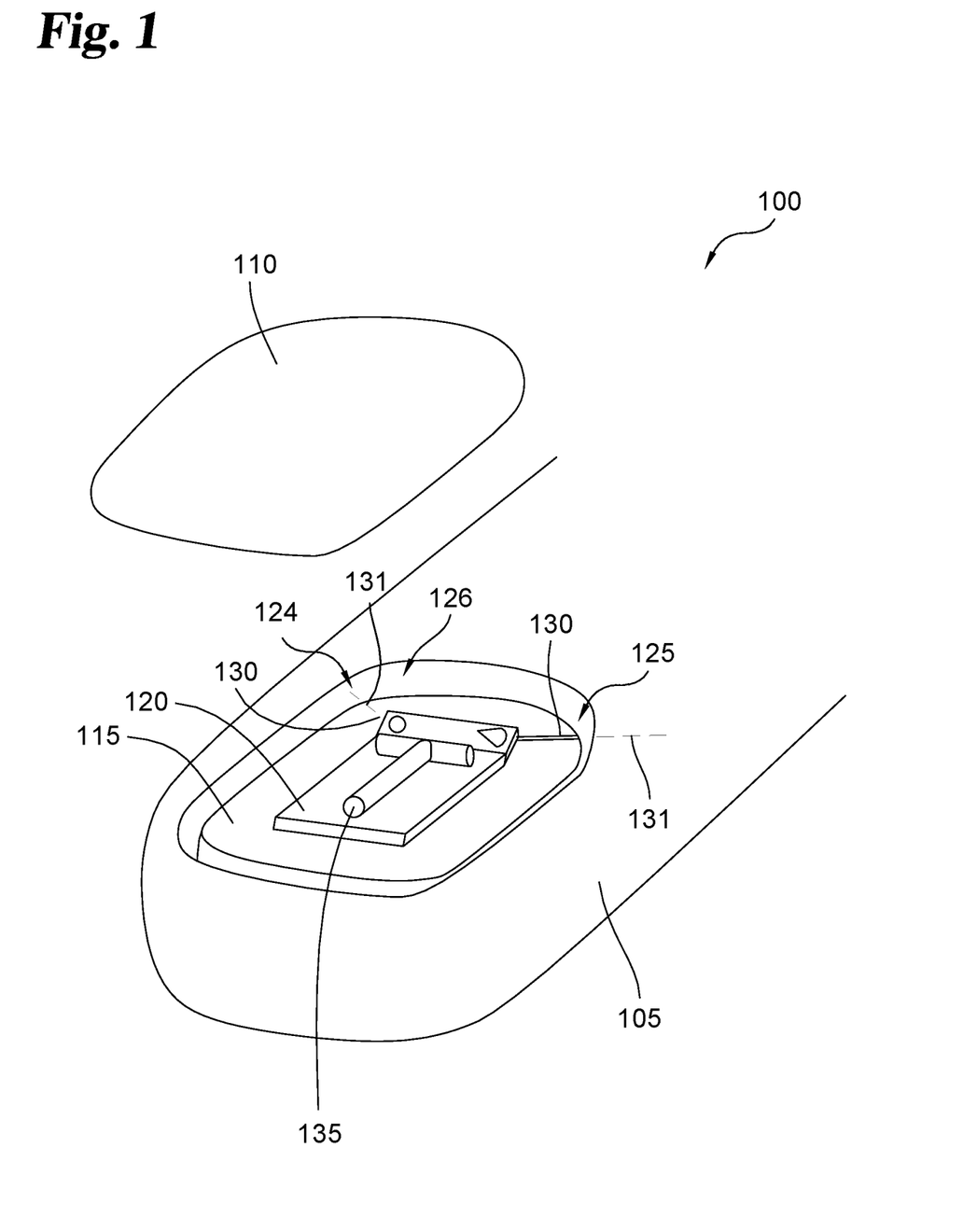
FIG. 1 is an exploded perspective view of one example of an assembly for mounting a prosthetic nail.

FIG. 1 illustrates at 100 one example of a system for mounting a prosthetic nail 110. The system shown at 100 includes at least one transdermal anchor 125 for retaining a nail mounting assembly like the one shown at 126 adjacent to or directly in contact with a digit 105. Transdermal anchor 125 includes an exterior portion 130 at an end of the anchor 125 that may be opposite an interior portion 131. The interior portion 131 of the transdermal anchor 125 may be referred to as "interior" because it may be positioned within the soft tissue of a digit 105, and may be placed in position by any suitable means such as by inserting the interior portion 131 under the skin of the digit. The interior portion 131 may be positioned within tissue of the digit and may be partially or fully surrounded by the soft tissue of the digit 105. Exterior portion 130 extends outside the tissue of the digit and may engage other portions of assembly 126. In this way, transdermal anchor provides support for assembly 126.

In another aspect, interior portion 131 of the transdermal anchor 125 may be configured to provide for and optionally encourage tissue growth around and through interior portion 131. This tissue growth can provide a more secure base for anchoring other parts of the assembly 126 thus reducing or eliminating the opportunity for assembly 126 to separate from digit 105.

Figure 2:
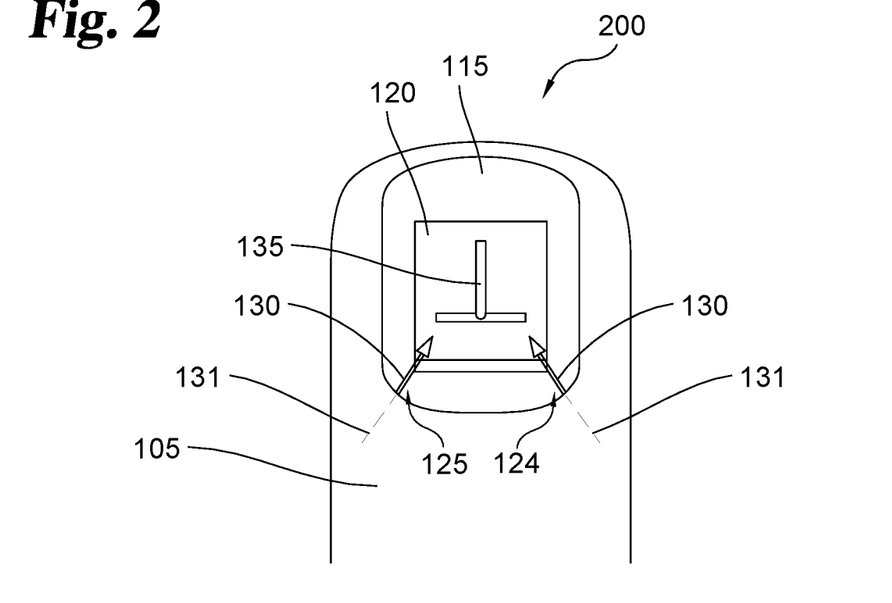
FIG. 2 is a top view of the assembly of FIG. 1.
Figure 3:
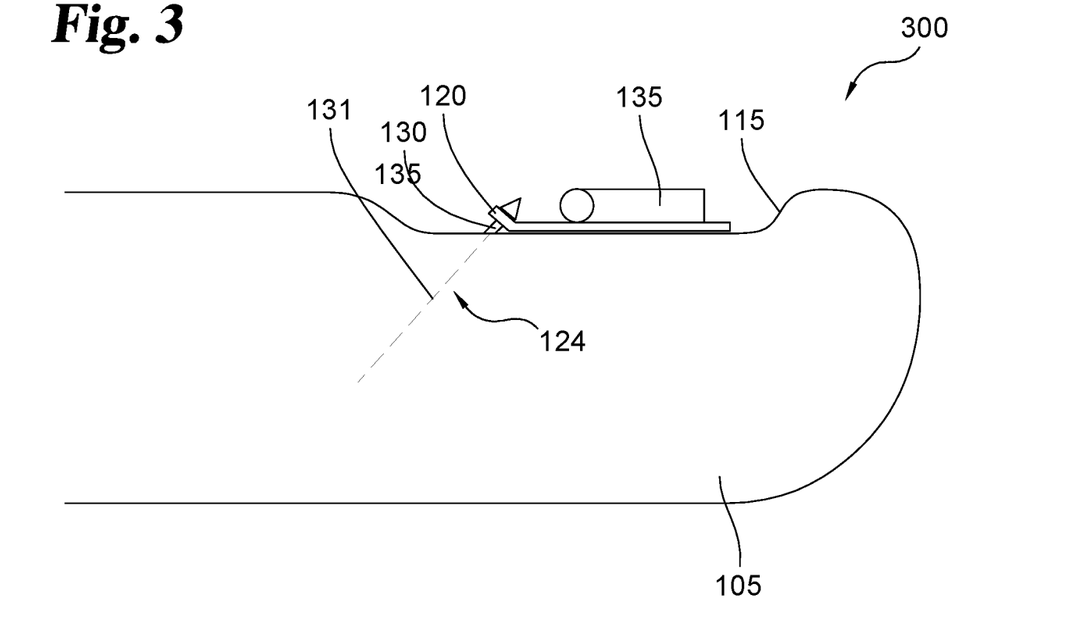
FIG. 3 is a side view of the assembly of FIGS. 1 and 2.

As shown in FIG. 1, this example provides a nail mounting assembly 126 positioned on the surface of a nail bed 115 and held in position by at least one transdermal anchor 125. The nail mounting assembly 126 optionally includes a base 120 and a mount 135. The base 120 may include at least one aperture such as a through opening located at the rear of nail mounting assembly 126. The aperture may be configured to receive at least one transdermal anchor 125 that optionally serves to anchor the nail mounting assembly 126 in place. The mount 135 may be attached to the top of the base 120 and may include projecting portions that are at right angles to one another and may define a recognizable shape such as a "T" shape as shown in FIG. 2. In one aspect, the projecting portions of mount 135 that have a "T" shaped may have a circular or round cross section as shown in FIG. 3.

The mount 135 may be configured to accept the nail 110 which may attach to the nail mounting assembly 126 via at least one "C" shaped friction fit or snap fit connector. The connector may surround at least a portion of the mount 135 in order to secure the nail 110 to the nail mounting assembly 126. In this way, the prosthetic nail 110 may be securely held in place adjacent to the mounting assembly 126.

FIG. 2 illustrates at 200 additional aspects of the system for mounting a prosthetic nail 100 first discussed in FIG. 1. The system for mounting a prosthetic nail 100 shares a number of components and functions in common with the one described before (see e.g., FIG. 1). For the sake of brevity as well as clarity, these common features will not be described in great detail below, but please refer to the previous discussion.

As illustrated in FIG. 2, the transdermal anchor 125 may be inserted into the soft tissue of the digit 105 with the interior portion 131 optionally extending diagonally outward. Optional diagonal positioning allows for the interior portion 131 of the transdermal anchor 125 to gain maximum exposure to the soft tissue of digit 105 provides for additional surface area contact with the surrounding tissue for added strength. In another aspect, the diagonal configuration may provide for additional resistance to lateral, rotational, or other strain on nail mounting assembly 126.

FIG. 3 illustrates at 300 another view of the system for mounting a prosthetic nail 100 discussed in FIGS. 1 and 2. As shown in FIG. 3, transdermal anchor 125 may be inserted into the soft tissue of the digit 105 diagonally downward and may angle proximately or distally. This configuration allows for the interior portion 131 of the transdermal anchor 125 to embed firmly within soft tissue of digit 105 providing an anchor for mounting assembly 126 while optionally avoiding avoid contact with bone structures in digit 105. In another aspect, this downward diagonal may assist in maintaining the nail mounting assembly 126 adjacent to nail bed 115, or optionally in direct contact with nail bed 115.

Figure 4:
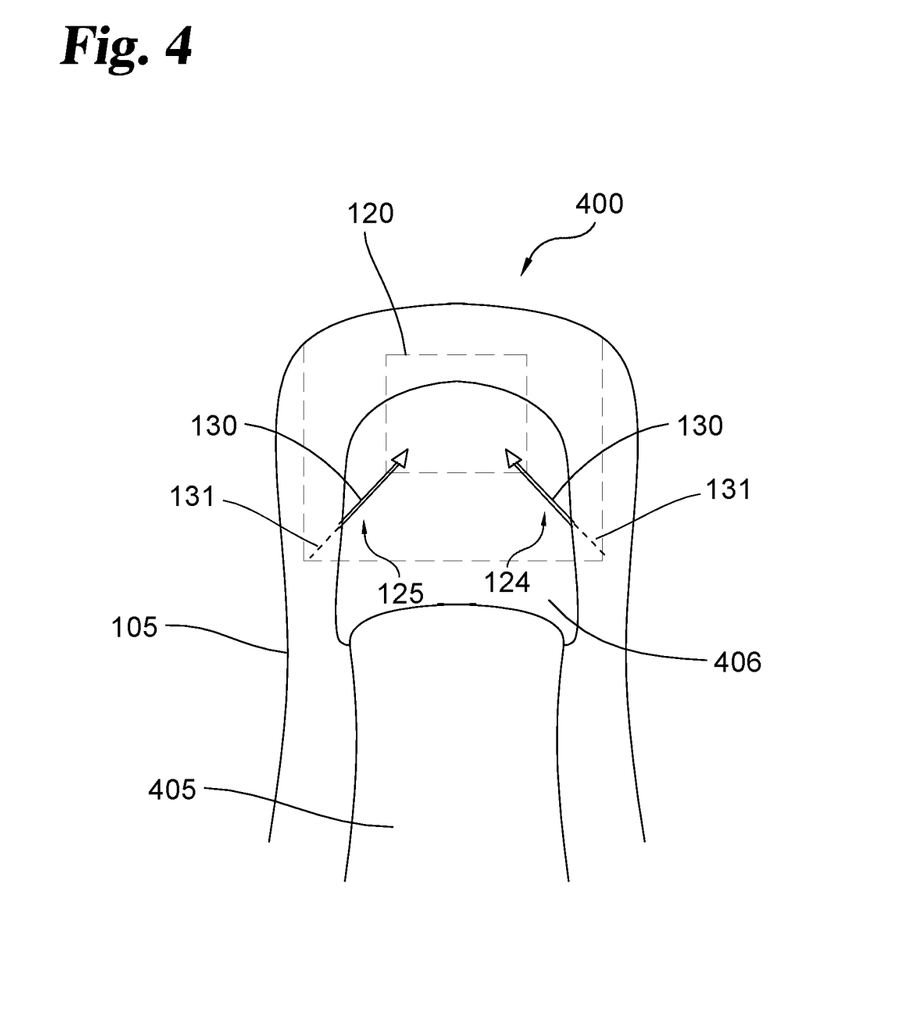
FIG. 4 is a cutaway view of a digit similar to the digit shown in the preceding figures.

FIG. 4 illustrates at 400 aspects of the relationship between the structure of digit 105, which is illustrated here a human toe, and the disclosed system for mounting a prosthetic nail. A proximal bone 405, such as a distal phalanx of a human toe, may be connected with a distal bone 406, and the distal bone 406 may be positioned directly beneath nail bed 115. In this example, the transdermal anchor 125 may be configured to angle outwardly toward the edge of digit 105 providing additional support against lateral movement between the nail mounting assembly 126 and nail bed 115. In another aspect, the outward diagonal positioning of transdermal anchors 124 and 125 provides for improved lateral support to maintain nail mounting assembly 126 in place without directly contacting bone structures he represented as bones 405 and 406.

Figure 5:
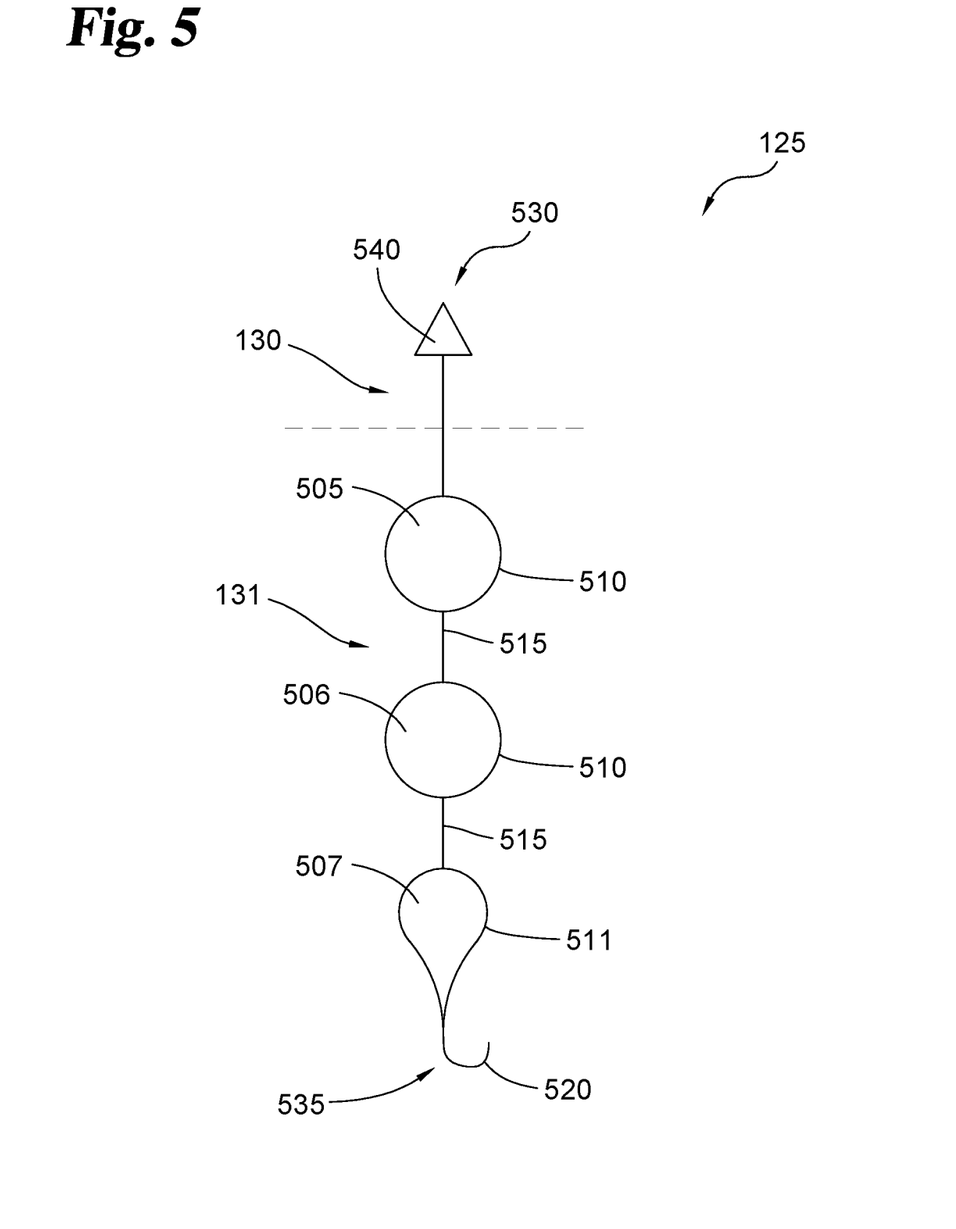
FIG. 5 is a component diagram illustrating aspects of a transdermal anchor like the one illustrated in the preceding figures.
Figure 6:
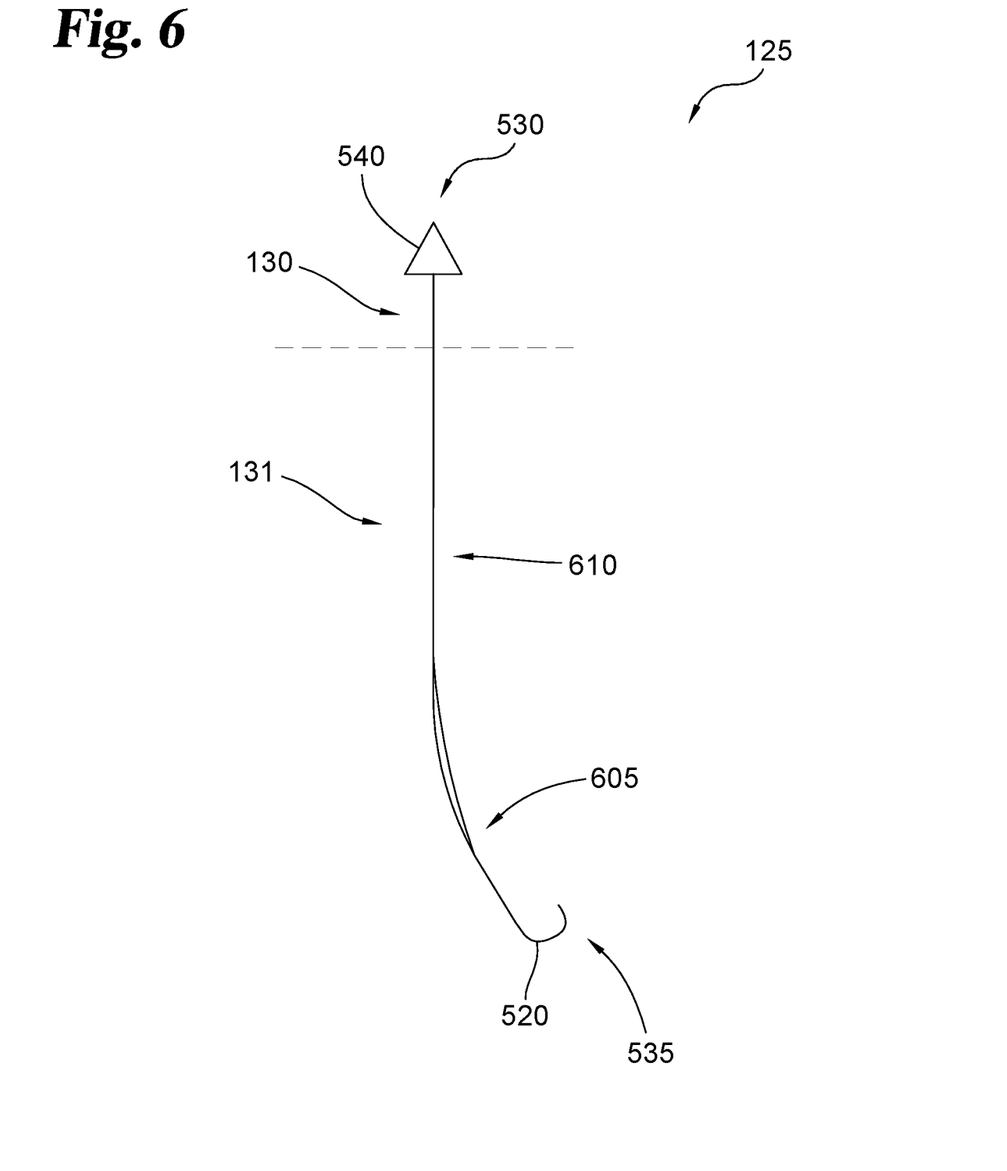
FIG. 6 is a component diagram illustrating aspects of the transdermal anchor of FIG. 5.

FIGS. 5 and 6 illustrate additional optional aspects that may be implemented in transdermal anchors 124 and 125. For example, in one aspect the interior portion 131 of transdermal anchor 125 optionally includes at least one through opening 505 which may be defined by a ring 510 located adjacent to a distal end 530 of transdermal anchor 125. The through opening 505 may be arranged and configured to accept soft tissue which may be introduced by any suitable means such as by allowing tissue to naturally grow into opening 505 over time. Soft tissue preferably engages the transdermal anchor by natural healing after insertion such that the tissue bonds together within through opening 505 as well as around the outside of ring 510. In another aspect, through opening 505 may be coupled to a second through opening 506 by at least one connecting element 515. Thus multiple rings 510 may be used in a transdermal anchor 125 to provide additional support as needed. In another aspect, rings 510, and 511 may be arranged and configured to be substantially planar and parallel to a common plane.

In another aspect, a tear-drop shaped ring 511 may be included at the proximal end of transdermal anchor 125. Ring 511 made define a teardrop shape through opening 507 which may be advantageous in providing easier insertion into the soft tissue during installation of the transdermal anchor 125. The tear-drop shaped through opening 507 may be also configured to accept the growth of soft tissue both around ring 511 and within through opening 507.

In another aspect, transdermal anchor 125 may include one or more arcuate extensions or barbs 520. These arcuate extensions 520 may be positioned at a proximal end 535 of transdermal anchor 125, or anywhere along rings 510, 511, or coupling elements 515. The arcuate extensions 520 may be useful in providing further strength and resistance to movement for transdermal anchor 125. The arcuate extension 520 may be made of a polymeric material that is substantially rigid thus possibly providing for easier insertion, while at the same time making it more difficult for transdermal anchor 125 to loosen from the surrounding soft tissue once inserted. In another aspect, the arcuate extension 520 of transdermal anchor 125 may be oriented parallel to a plane that is also parallel to the rings 510 and 511.

The exterior portion 130 of the transdermal anchor 125 may include a retention member 540. The retention member 540 serves as an optional coupler or attachment member for securing transdermal anchor 125 to the base 120. In one aspect, the retention member 540 may be generally conical in shape and may be inserted through an aperture in the base 120, wherein the aperture may be slightly narrower or smaller than the widest portion of retention member 540 thus allowing the base 120 to firmly retain retention member 540 in place.

FIG. 6 shows additional optional aspects of the transdermal anchor 125 discussed above in FIG. 5. The transdermal anchor 125 may include an angled portion 605 that angles away from the remaining portion 610. The angled portion 605 may be so angled to allow for the transdermal anchor 125 to avoid contact with bone structures of the digit the transdermal anchor is mounted to. In another aspect, the arcuate extension 520 of transdermal anchor 125 may be oriented in perpendicularly to rings 510 and 511. In this example, rings 510 and 511 may be arranged parallel to a common plane, and extension 520 may be substantially perpendicular to this common plane as shown, thus providing additional support for transdermal anchor 125.

Figure 7:
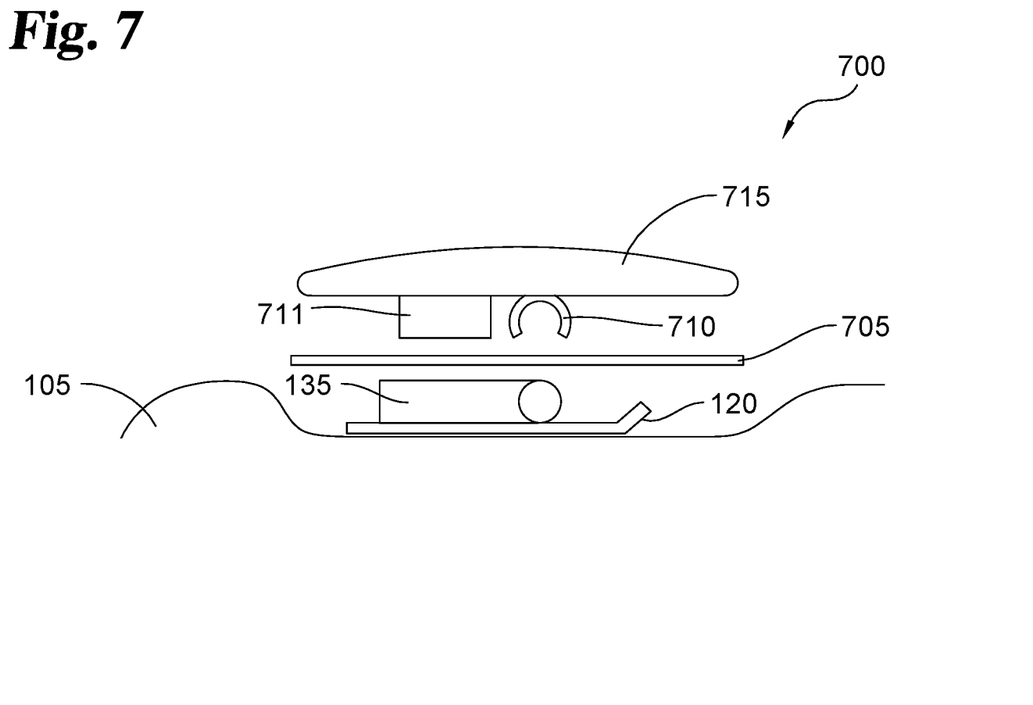
FIG. 7 is an exploded side view of another example of an assembly for mounting a prosthetic nail.
Figure 8:
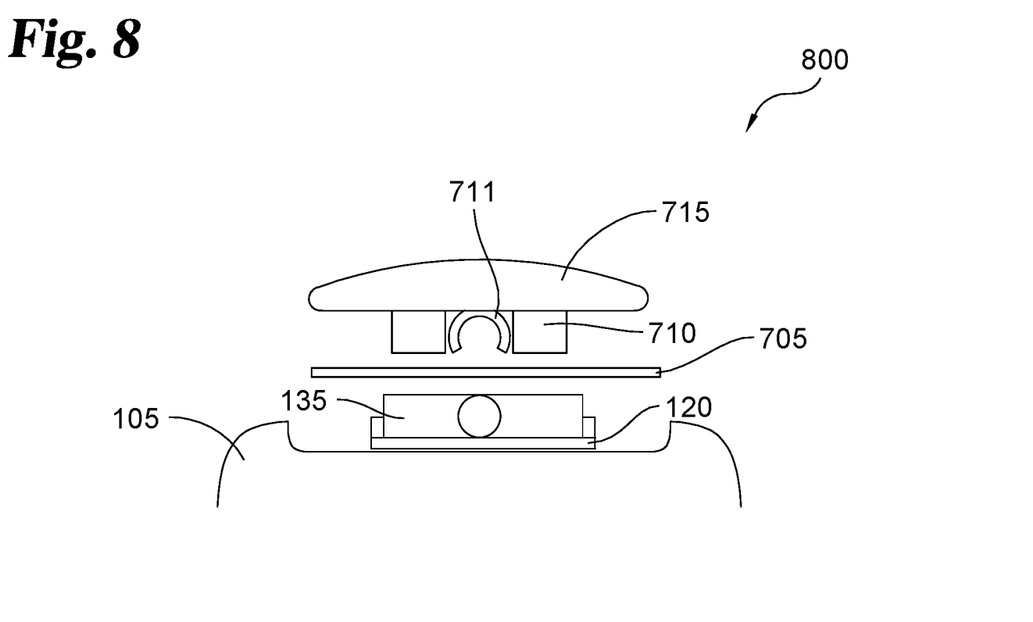
FIG. 8 is an exploded front view of the assembly of FIG. 7.
Figure 9:
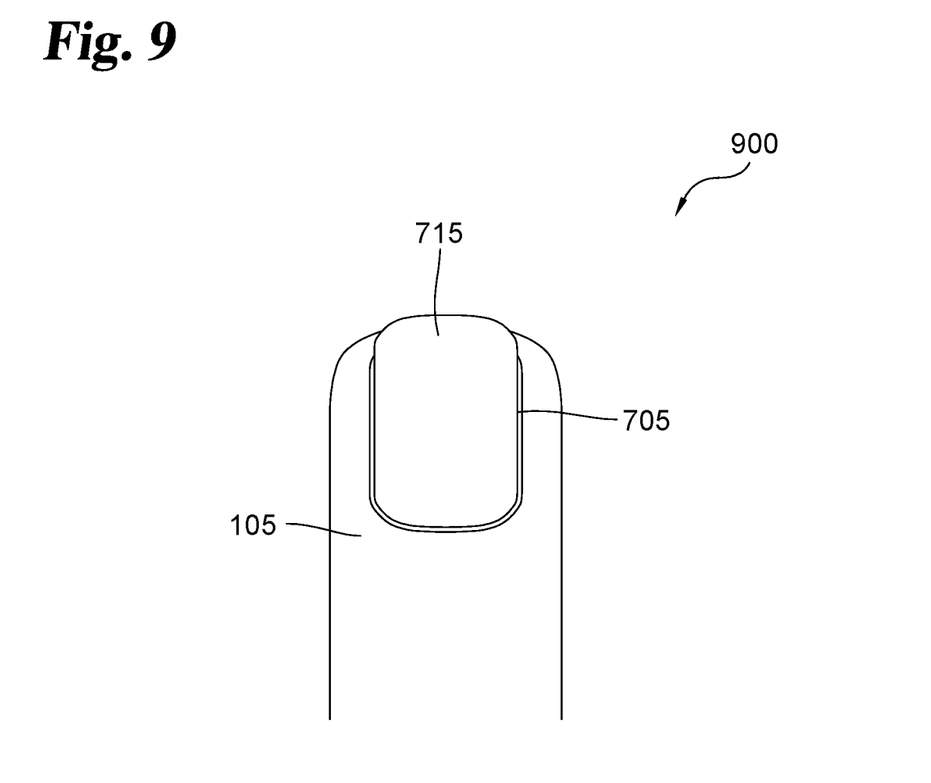
FIG. 9 is a top view of the assembly of FIGS. 7 and 8.

FIGS. 7, 8, and 9 illustrate at 700 additional aspects of the disclosed system for mounting a prosthetic nail. A prosthetic nail 715 similar to nail 110 is shown that includes at least one first coupler 710 and at least one second coupler 711. Mount 135 includes one or more protrusions extending away from the base that are arranged to engage multiple couplers on the prosthetic nail 715. In this example, first coupler 710 and second coupler 711 are "C" shaped and configured to snap fit into place by engaging one or more of the protruding portions of mount 135. Thus nail 715 may be mounted to base 120 by positioning nail 715 two engage with mount 135 and applying gentle pressure in the direction of digit 105 until couplers 710 and 711 snap into place.

In another aspect, a protective layer 705 may be positioned between nail 715 and digit 105. The protective layer 705 may be made of a polymeric material that is somewhat pliable such as rubber or a silicone. The protective layer 705 may serve as a protective barrier between the skin of digit 105 and the edges of prosthetic nail 715 and may thus reduce or eliminate the opportunity for chafing or scarring caused by nail 715. In another aspect, the protective layer 705 may reduce or eliminate gaps between the prosthetic nail 715 and the nail bed, or skin of the digit thus reducing the opportunity for debris to enter the space between nail 715 and the nail bed. In another aspect, protective layer 705 may have cosmetic advantages such as providing enhanced or more natural blended appearance to the prosthetic nail 715 illustrates. FIG. 9 shows the complete system for mounting a prosthetic nail 100 discussed in FIGS. 7 and 8.

Additional configurations of the disclosed system are provided in the following numbered examples:

Example 1

An apparatus comprising a transdermal anchor with an interior portion and an exterior portion, wherein the interior portion is positioned within tissue of a digit, and the exterior portion extends outside the tissue of the digit.

Example 2

The apparatus of Example 1, comprising an exterior base positioned on a nail bed of the digit, wherein the exterior base is coupled to the exterior portion of the transdermal anchor.

Example 3

The apparatus according to any previous example, wherein the exterior base includes a mount for coupling the base to a prosthetic nail.

Example 4

The apparatus according to any previous example, wherein the interior portion defines a through opening for capturing surrounding tissue of the digit.

Example 5

The apparatus according to any previous example, wherein the interior portion defines multiple through openings, and one of the through openings may be tear-drop shaped.

Example 6

The apparatus according to any previous example, wherein the interior portion includes an arcuate extension at a proximal end of the interior portion for capturing surrounding tissue.

Example 7

The apparatus according to any previous example, wherein the interior portion includes an angled section angled outwardly to offset a remaining section of the interior portion away from a distal phalanx of the digit.

Example 8

The apparatus according to any previous example, wherein the interior portion may be free from direct bone contact in the digit.

Example 9

The apparatus according to any previous example, wherein the transdermal anchor may be made of a material that includes a rigid polymeric material.

Example 10

The apparatus according to any previous example, wherein the transdermal anchor may be made primarily of polyetheretherketone.

Example 11

The apparatus according to any previous example, wherein the exterior base includes a mount for coupling the base to a prosthetic nail.

Example 12

The apparatus according to any previous example, wherein the exterior base mount includes protrusions extending away from the base that are arranged to engage multiple couplers on the prosthetic nail.

Example 13

The apparatus according to any previous example, wherein the protrusions include multiple portions at right angles to each other.

Example 14

The apparatus according to any previous example, wherein the exterior base includes couplers for engaging corresponding retention members at a distal end of the external portion of the transdermal anchor.

Example 15

The apparatus according to any previous example, wherein the exterior base portion may be made of a base material that includes a pliable polymeric material.

Example 16

The apparatus according to any previous example, wherein the implant includes multiple transdermal anchors adjacent to the nail.

Example 17

The apparatus according to any previous example, wherein a layer of pliable polymeric material surrounds the prosthetic nail and is positioned between the prosthetic nail and the mount.

Example 18

A transdermal anchor that has an interior portion and an exterior portion, wherein the interior portion is positioned within tissue of a digit, and the exterior portion extends outside the tissue of the digit, and wherein the interior portion defines a through opening for capturing surrounding tissue of the digit.

Example 19

The transdermal anchor of example 18, wherein the interior portion defines multiple through openings, and one of the through openings is tear-drop shaped.

Example 20

The transdermal anchor of any one of examples 18-19, wherein the interior portion includes an angled section angled outwardly to offset a remaining section of the interior portion away from a distal phalanx of the digit.

Example 21

The transdermal anchor of any one of examples 18-20, wherein the interior portion includes an arcuate extension at a proximal end of the interior portion for capturing surrounding tissue.

Example 22

The transdermal anchor of any one of examples 18-21, wherein the interior portion is free from direct bone contact in the digit.

Example 23

The transdermal anchor of any one of examples 18-22, wherein the transdermal anchor is made of a material that includes a rigid polymeric material.

Example 24

The transdermal anchor of any one of examples 18-23, wherein the transdermal anchor is made primarily of polyetheretherketone.

Example 25

The transdermal anchor of any one of examples 18-24, comprising:
an exterior base positioned on a nail bed of the digit, wherein the exterior base is coupled to the exterior portion of the transdermal anchor.

Example 26

The transdermal anchor of any one of examples 18-25, wherein the exterior base includes a mount for coupling the base to a prosthetic nail.

Example 27

The transdermal anchor of any one of examples 18-26, wherein the mount of the exterior base includes protrusions extending away from the base that are arranged to engage multiple couplers on the prosthetic nail.

Example 28

The transdermal anchor of any one of examples 18-27, wherein the protrusions include multiple portions at right angles to each other.

Example 29

The transdermal anchor of any one of examples 18-28, wherein the exterior base includes couplers for engaging corresponding retention members at a distal end of the external portion of the transdermal anchor.

Glossary of Definitions and Alternatives

While the invention may be illustrated in the drawings and described herein, this disclosure may be to be considered as illustrative and not restrictive in character. The present disclosure may be exemplary in nature and all changes, equivalents, and modifications that come within the spirit of the invention are included. The detailed description may be included herein to discuss aspects of the examples illustrated in the drawings for the purpose of promoting an understanding of the principles of the invention. No limitation of the scope of the invention may be thereby intended. Any alterations and further modifications in the described examples, and any further applications of the principles described herein are contemplated as would normally occur to one skilled in the art to which the invention relates. Some examples are disclosed in detail, however some features that may not be relevant may have been left out for the sake of clarity.

Where there are references to publications, patents, and patent applications cited herein, they are understood to be incorporated by reference as if each individual publication, patent, or patent application were specifically and individually indicated to be incorporated by reference and set forth in its entirety herein.

Singular forms "a", "an", "the", and the like include plural referents unless expressly discussed otherwise. As an illustration, references to "a device" or "the device" include one or more of such devices and equivalents thereof.

Directional terms, such as "up", "down", "top" "bottom", "fore", "aft", "lateral", "longitudinal", "radial", "circumferential", etc., are used herein solely for the convenience of the reader in order to aid in the reader's understanding of the illustrated examples. The use of these directional terms does not in any manner limit the described, illustrated, and/or claimed features to a specific direction and/or orientation.

Multiple related items illustrated in the drawings with the same part number which are differentiated by a letter for separate individual instances, may be referred to generally by a distinguishable portion of the full name, and/or by the number alone. For example, if multiple "laterally extending elements" 90A, 90B, 90C, and 90D are illustrated in the drawings, the disclosure may refer to these as "laterally extending elements 90A-90D," or as "laterally extending elements 90," or by a distinguishable portion of the full name such as "elements 90". The language used in the disclosure are presumed to have only their plain and ordinary meaning, except as explicitly defined below. The words used in the definitions included herein are to only have their plain and ordinary meaning. Such plain and ordinary meaning may be inclusive of all consistent dictionary definitions from the most recently published Webster's and Random House dictionaries. As used herein, the following definitions apply to the following terms or to common variations thereof (e.g., singular/plural forms, past/present tenses, etc.):

"Aperture" generally refers to an opening or open space defined by a structure that at least partially surrounds the aperture. An aperture may be of any shape such as, without limitation, a circle, square, or other closed polygon. For example, a hole passing through a solid object may be thought of as an aperture.

In another aspect, an aperture may be not fully surrounded by the defining structure such as in the case of a "U"-shaped structure having a gap in at least one side of the structure.

"Arcuate" generally refers to a curved shape, such as in the case of a portion of a circle, or other curved surface or line.

"Digit" generally refers to the most distal parts of a limb of an animal or human. In one example, humans normally have five digits on each extremity, and may be colloquially referred to on the hand as "fingers" and on the foot as "toes". Each digit may be formed by several bones called phalanges, surrounded by soft tissue. Human digits normally have a nail at the distal phalanx. The phenomenon of polydactyly occurs when extra digits are present, and oligodactyly occurs when fewer than the normal number of digits may be present.

In another example, some animals have a single digit at the extremity of their limbs such as in the case of a horse hoof, two digits, such as in the case of a goat or a cow, or four or five digits such as in the case of a dog. Digits of animals may include one or more phalanges bearing a nail or claw.

"Distal" generally refers to the most distant or the more distant of two or more things. For example, the distal end of the femur may be the end just above the knee.

"Distal phalanx" generally refers to the toe bones of the foot that are articulate with the intermediate phalanges. The distal phalanx provides the home for both the toenail and the fleshy pad located on the underside of each toe. They are the last bone at the end of the toe.

"Nail bed" generally refers to the formative layer of cells at the base of a fingernail or toenail. Also, the layer of tissue that may be underneath the nail and may be extremely sensitive.

"Prosthetic" generally refers to an artificial device designed to replace a missing body part. This body part may be lost through trauma, disease, or a condition present at birth. Prosthetics are intended to restore the normal functions of the missing body part.

"Proximal end" generally refers to the end that may be towards the beginning or nearer to the item in question. For example, the proximal end of the femur may be part of the hip joint. The opposite of proximal may be distal.

"Tear-drop shape" generally refers to a shape with two straight side portions diverging at an acute angle from a lower point and an arcuate upper portion extending between the upper ends of the side portions.

"Transdermal Anchor" generally refers to a device or assembly passing into the body from outside the body for the purpose of keeping some other object from moving. The portion of the transdermal anchor that may be inside the body may optionally be coupled to other internal body structures such as bones, muscle tissue, cartilage, and the like.

REFERENCE NUMBERS

100 system for mounting a prosthetic nail
105 digit
110 nail
115 nail bed
120 base
124 transdermal anchor
125 transdermal anchor
126 nail mounting assembly
130 exterior portion
131 interior portion
135 mount
405 proximal bone
406 distal bone
505 through opening
507 tear-drop shaped through opening
510 ring
511 ring
515 coupling element
520 arcuate extension
530 distal end
535 proximal end
540 retention member
605 angled portion
610 main portion
615 arcuate extension
705 protective layer
710 first coupler
711 second coupler
715 prosthetic nail What may be claimed is:

1. A prosthetic nail mount assembly, comprising:
a transdermal anchor with an interior portion and an exterior portion, wherein the interior portion is sized and configured to be positioned within tissue of a digit, and the exterior portion extends outside the tissue of the digit; and
an exterior base sized and configured to be directly positioned on a nail bed of the digit, wherein the exterior base is coupled to the exterior portion of the transdermal anchor;
wherein the exterior base includes a mount for removably coupling the base to a prosthetic nail, wherein the mount of the exterior base includes protrusions extending away from the base that are arranged to engage multiple couplers on the prosthetic nail; and
wherein the interior portion is free from direct bone contact in the digit.

2. The mount assembly of claim 1, wherein the interior portion defines a through opening for capturing surrounding tissue of the digit.

3. The mount assembly of claim 2, wherein the interior portion defines multiple through openings, and one of the through openings is tear-drop shaped.

4. The mount assembly of claim 1, wherein the interior portion includes an arcuate extension at a proximal end of the interior portion for capturing surrounding tissue.

5. The mount assembly of claim 1, wherein the interior portion includes an angled section angled outwardly to offset a remaining section of the interior portion away from a distal phalanx of the digit.

6. The mount assembly of claim 1, wherein the transdermal anchor is made of a material that includes a rigid polymeric material.

7. The mount assembly of claim 6, wherein the transdermal anchor is made primarily of polyetheretherketone.

8. The mount assembly of claim 1, wherein the protrusions include multiple portions at right angles to each other.

9. The mount assembly of claim 1, wherein the exterior base includes couplers for engaging corresponding retention members at a distal end of the exterior portion of the transdermal anchor.

10. The mount assembly of claim 1, wherein the exterior portion is made of a material that includes a pliable polymeric material.

11. The mount assembly of claim 1, comprising:
one or more additional transdermal anchors adjacent to the nail, wherein the one or more additional transdermal anchors has an interior portion and an exterior portion, wherein the interior portion is sized and configured to be positioned within tissue of the digit, and the exterior portion extends outside the tissue of the digit.

12. The mount assembly of claim 1, wherein a layer of pliable polymeric material surrounds the prosthetic nail and is positioned between the prosthetic nail and the mount.

* * * * *